United States Patent
Hayman

(10) Patent No.: US 11,351,099 B2
(45) Date of Patent: Jun. 7, 2022

(54) SKINCARE REJUVENATION COMPOSITION AND METHOD OF MANUFACTURE

(71) Applicant: Hillary Hayman, Los Angeles, CA (US)

(72) Inventor: Hillary Hayman, Los Angeles, CA (US)

(73) Assignee: ELYSE ENTERPRISES LLC, Los Angeles, CA (US)

( * ) Notice: Subject to any disclaimer, the term of this patent is extended or adjusted under 35 U.S.C. 154(b) by 0 days.

(21) Appl. No.: 17/013,031

(22) Filed: Sep. 4, 2020

(65) Prior Publication Data

US 2022/0071870 A1 Mar. 10, 2022

(51) Int. Cl.
  *A61K 8/34* (2006.01)
  *A61K 8/365* (2006.01)
  *A61K 8/73* (2006.01)
  *A61Q 19/10* (2006.01)
  *A61Q 19/08* (2006.01)
  *A61Q 17/04* (2006.01)

(52) U.S. Cl.
CPC .............. *A61K 8/342* (2013.01); *A61K 8/365* (2013.01); *A61K 8/735* (2013.01); *A61Q 17/04* (2013.01); *A61Q 19/08* (2013.01); *A61Q 19/10* (2013.01); *A61K 2800/28* (2013.01); *A61K 2800/30* (2013.01)

(58) Field of Classification Search
None
See application file for complete search history.

(56) References Cited

U.S. PATENT DOCUMENTS

| 5,665,364 | A | 9/1997 | McAtee et al. | |
|---|---|---|---|---|
| 7,396,526 | B1* | 7/2008 | Cole | A61K 8/365 424/400 |
| 2008/0132585 | A1 | 6/2008 | Miyata et al. | |
| 2015/0050324 | A1* | 2/2015 | Florence | A61K 8/9789 424/401 |

(Continued)

FOREIGN PATENT DOCUMENTS

| CA | 2534372 A1 | 2/2005 |
|---|---|---|
| WO | 2001085129 A2 | 11/2001 |

OTHER PUBLICATIONS

Anchisi et al 'Stability studies of new cosmetic formulations with vegetable extracts as functional agents' II Farmaco, 2001, vol. 56, pp. 427-431.

(Continued)

*Primary Examiner* — Nicole P Babson
(74) *Attorney, Agent, or Firm* — Dickinson Wright PLLC

(57) ABSTRACT

A skincare rejuvenation composition, adapted at least for tactile use, consists essentially of a skincare rejuvenation ingredient, a skin exfoliation ingredient, an acidity balancing ingredient, a sunscreen composition and an emulsifier. The skincare rejuvenation ingredient has a first weight percentage, the skin exfoliation ingredient has a second weight percentage, and the acidity balancing ingredient has a third weight percentage, whereby each of the first weight percentage, the second weight percentage, and the third weight percentage are substantially equal. As an example, the skincare rejuvenation ingredient may be retinol, the skin exfoliation ingredient may be glycolic acid, and the acidity balancing ingredient may be hyaluronic acid.

17 Claims, 4 Drawing Sheets

(56) References Cited

U.S. PATENT DOCUMENTS

2017/0128357 A1   5/2017   Brillouet et al.
2017/0312215 A1   11/2017  Patel

OTHER PUBLICATIONS

International Search Report and Written Opinion for PCT/US2020/049626, dated Feb. 4, 2021.
Wikipedia 'Emulsion' Mar. 29, 2019 (Mar. 29, 2019).
Zoe Weiner 'Yep, You Can Use Both Glycolic Acid and Retinol on Your Skin' Dec. 26, 2018 (Dec. 26, 2018) retreived from ,https://www.wellandgood.com/can-glycolic-acid-and-retinol-be-used-together/>.

* cited by examiner

SKINCARE REJUVENATION COMPOSITION AND METHOD OF MANUFACTURE

BACKGROUND

1. Field

This disclosure generally relates to skincare. More particularly, the disclosure relates to compositions adapted for use on the skin of a user.

2. General Background

Skincare creams abound online web portals and the shelves of brick-and-mortar stores, often making lofty claims about their effectiveness in promoting anti-aging. For example, skincare cream manufacturers and distributors will typically say that their products improve the appearance of wrinkles, fine lines, and discoloration. Some will even go so far as to name their skincare products after a particular substance, such as Retinol, which is understood by some consumers to have skincare rejuvenation properties.

Yet, the ingredient list for the vast majority of skincare products is typically a long list of potentially harmful chemicals, rather than being limited to one particular ingredient. For instance, a product labeled as a Retinol product will typically have over twenty to thirty different ingredients, of which Retinol is only one. One of those additional ingredients is typically cyclopentasiloxane, which has raised concerns about the potential for hormone disruption in the human body. Yet another additional ingredient is dimethicone, which has led some users to have more acne from drying of the skin. The foregoing examples are only a select few of many potentially harmful ingredients that are included in many skincare products along with a more natural ingredient, such as Retinol.

Furthermore, many of these products have ingredients that contraindicate another ingredient. For example, vitamin C is a common ingredient in creams with Retinol, yet it has been shown to diminish the skincare rejuvenation effects of Retinol.

Accordingly, current compositions and processes often involve many, sometimes potentially harmful, ingredients that have diminished effectiveness based on contraindications.

SUMMARY

In one embodiment, a skincare rejuvenation composition, adapted at least for tactile use, consists essentially of a skincare rejuvenation ingredient, a skin exfoliation ingredient, an acidity balancing ingredient, a sunscreen composition, a solvent, a carrier oil, and an emulsifier. The skincare rejuvenation ingredient has a first weight percentage, the skin exfoliation ingredient has a second weight percentage, and the acidity balancing ingredient has a third weight percentage, whereby each of the first weight percentage, the second weight percentage, and the third weight percentage are substantially equal.

As an example, the skincare rejuvenation ingredient may be retinol, the skin exfoliation ingredient may be glycolic acid, and the acidity balancing ingredient may be hyaluronic acid.

In another embodiment, a method of manufacture is provided for composing the foregoing skincare rejuvenation composition.

BRIEF DESCRIPTION OF THE DRAWINGS

The above-mentioned features of the present disclosure will become more apparent with reference to the following description taken in conjunction with the accompanying drawings wherein like reference numerals denote like elements and in which.

DETAILED DESCRIPTION

Figure 1A:
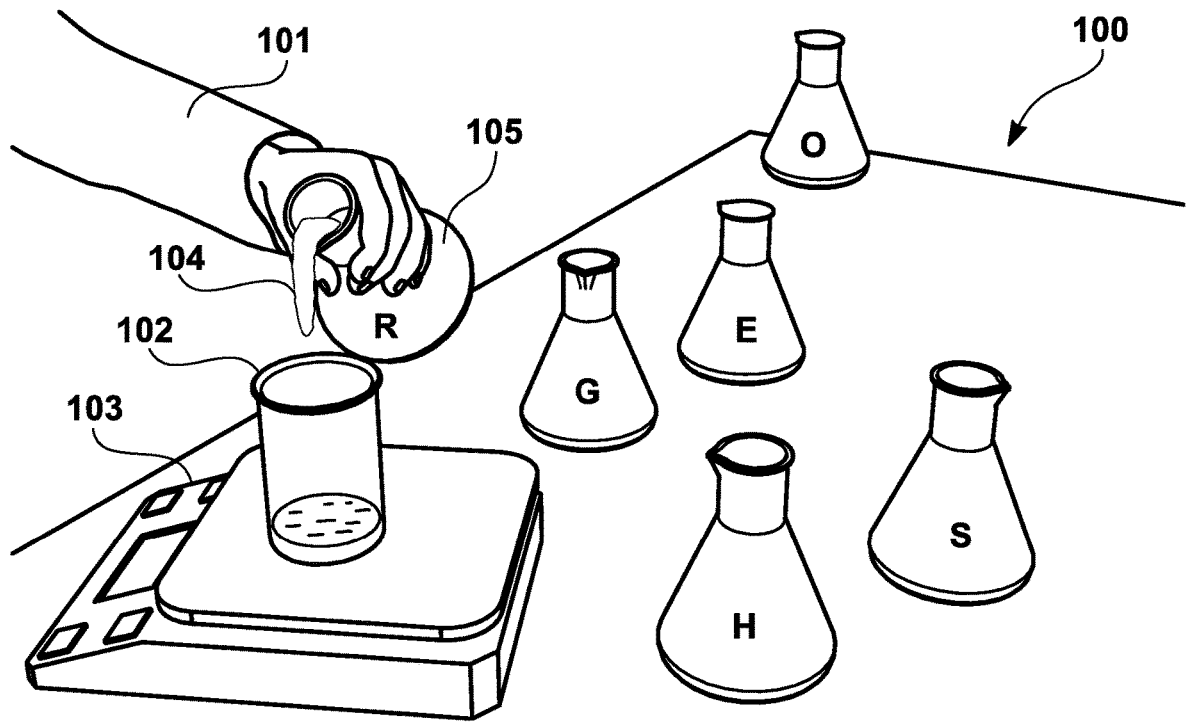
FIG. 1A illustrates the user weighing a beaker on a scale while pouring retinol into the beaker from a retinol flask.

A skincare rejuvenation composition is adapted for tactile use. Rather than having a myriad of different ingredients with potentially harmful effects and contraindications, the skincare rejuvenation composition has a limited number of ingredients, which work together in a balanced manner to promote skincare rejuvenation.

For instance, the skincare rejuvenation composition may have one ingredient to promote skincare rejuvenation, one ingredient to exfoliate the skin, one ingredient to balance acidity, and one ingredient to protect the skin from sun exposure. Additionally, the skincare rejuvenation composition may have a carrier oil for the ingredients, as well as a solvent. The skincare rejuvenation composition may also have an emulsifier that acts as a binding agent of the foregoing ingredients. In essence, the emulsifier provides a smooth texture for the composition.

Furthermore, the skincare rejuvenation composition may specifically exclude ingredients that would provide contraindications to the foregoing ingredients. For example, vitamin C is specifically excluded from the ingredient list to avoid a contraindication with the ingredient that promotes skincare rejuvenation.

Additionally, the ingredient list is specifically limited to a relatively small number of ingredients to minimize the number of chemicals applied to the skin of a user, thereby reducing the risk of possible negative skin reactions (e.g., drying out of skin, redness, etc.). For instance, the ingredients may be limited to a range of three to eight ingredients. (Other ranges may be used instead.) Accordingly, the skincare rejuvenation composition may avoid the myriad of harmful ingredients typically found in conventional skincare products.

In one embodiment, the skincare rejuvenation composition also avoids the need for multiple skincare creams. A common skincare approach is to have one cream for skincare rejuvenation and one cream for sun exposure protection. The skincare rejuvenation composition avoids the need for multiple creams by having one cream that performs both skincare rejuvenation and sun exposure protection.

Finally, the skincare composition may have a balanced blend of ingredients. In other words, certain core ingredients may have an equal, or substantially equal, weight percentage as other ingredients. (The term "substantial" is intended to mean a deviation within a predetermined threshold, such as, for example, zero to twenty percent.) The phrase "core ingredients" refer to ingredients that form the basis for skincare rejuvenation, rather than ancillary ingredients such as carrier agents or emulsifiers. For example, the ingredient that promotes skincare rejuvenation may have an equal weight percentage as to the ingredient that exfoliates the skin and the ingredient that balances acidity. Having such a balanced blend of core ingredients has been discovered to help reduce the possibility of negative skin reactions, which may occur as a result of an imbalance in the weight percentages of such core ingredients. In one embodiment, the ingredient that protects the skin from sun exposure may also be in an equal, or substantially equal, weight percentage as to the remainder of the ingredients. In another embodiment, the ingredient that protects the skin from sun exposure may have a lesser or greater weight percentage than the remainder of the ingredients. Finally, the emulsifier may have an equal, substantially equal, lesser, or greater weight percentage as compared to the remainder of the ingredients.

As an example, the ingredients of the skincare rejuvenation composition may be as follows: retinol (ingredient that promotes skincare rejuvenation), glycolic acid (ingredient that exfoliates the skin), hyaluronic acid (ingredient that balances acidity), a sunscreen composition (ingredient that protects the skin from sun exposure), a carrier oil (e.g., coconut oil, avocado oil, almond oil, olive oil, etc.) and an emulsifier. The sunscreen composition may have a sun protection factor ("SPF") of thirty, or higher, to protect the skin from sun exposure. Furthermore, the sunscreen composition may have one or more ingredients, such as titanium dioxide, zinc oxide, avobenzone, and/or Mexoryl™ sx (encamsule or Terephthalylidene dicamphor sulfonic acid) that are generally deemed to be safe, specifically in avoiding negative skin reactions. Finally, the emulsifier may be an ionic emulsifier (e.g., aloe, seaweed extract, etc.), a non-ionic emulsifier (e.g. polysorbate 80 or polysorbate 20), a liquid crystal emulsifier (e.g., lecithin), a polymeric emulsifier, or the like.

An example of the formula for the skincare rejuvenation composition is provided the following table (expressed in weight percentage):

| Ingredient | Wt % |
| --- | --- |
| Retinol | 2 |
| Glycolic Acid | 2 |
| Hyaluronic Acid | 2 |
| Sunscreen Composition SPF 30 | 14 |
| Water | 40 |
| Coconut Oil | 35 |
| Polysorbate 80 | 5 |

In the foregoing example, retinol, glycolic acid, and hyaluronic acid have an equal weight percentage, given that they are considered core ingredients. Since the maximum weight percentage deemed to be acceptable for retinol-based consumer products is two percent, the weight percentage is established at two percent. Accordingly, the weight percentage may be two percent or less. In essence, the equal weight percentages of these three ingredients allow for skincare rejuvenation, exfoliation, and acidity balancing with reduced potential for negative reactions. Although the weight percentage of retinol cannot exceed two percent, the weight percentages of the other core ingredients may each exceed two percent, while still being substantially equal (e.g., within a weight deviation of thirty percent or less).

Additionally, the sunscreen composition may have a higher or substantially equal weight percentage to the foregoing ingredients. In one embodiment, the skincare rejuvenation composition may be formulated without the sunscreen composition.

Although water is depicted as the solvent, various other solvents (e.g., glycerin, propylene glycol, etc.) may be utilized instead. The solvent may make up zero to ninety percent by weight of the skincare rejuvenation composition.

Furthermore, coconut oil is depicted only as an example of a carrier oil; other carrier oils, or no carrier oil, may be used.

Finally, an emulsifier, such as polysorbate 80, may have a significantly higher weight percentage than the core ingredients to bind all of the ingredients together. In particular, the emulsifier may have a weight percentage in the range of five to fifteen percent. (Other ranges for the emulsifier may be utilized instead.)

The example provided above is only intended as an example, given that different types of ingredients and weight percentages may be utilized instead. Furthermore, different core ingredients may be utilized. For example, the core ingredients may include retinol and glycolic acid without hyaluronic acid, or retinol and hyaluronic acid without glycolic acid.

Figure 1B:
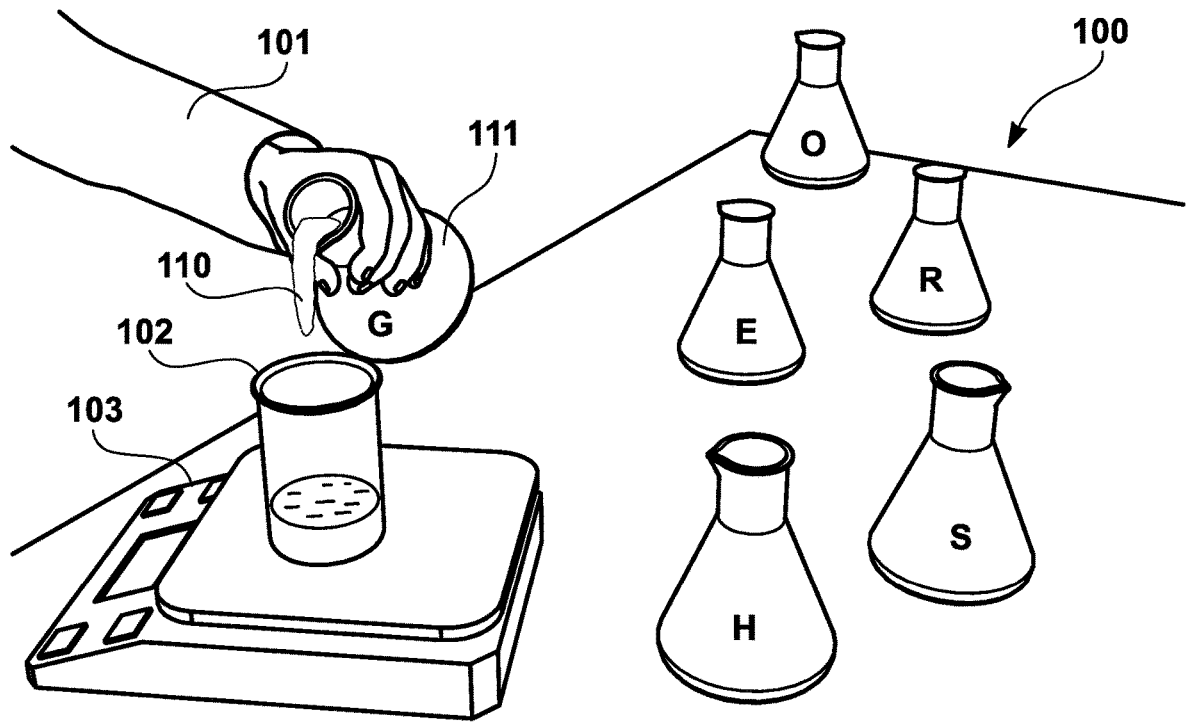
FIG. 1B illustrates the user adding glycolic acid to the beaker from a glycolic acid flask.
Figure 1C:
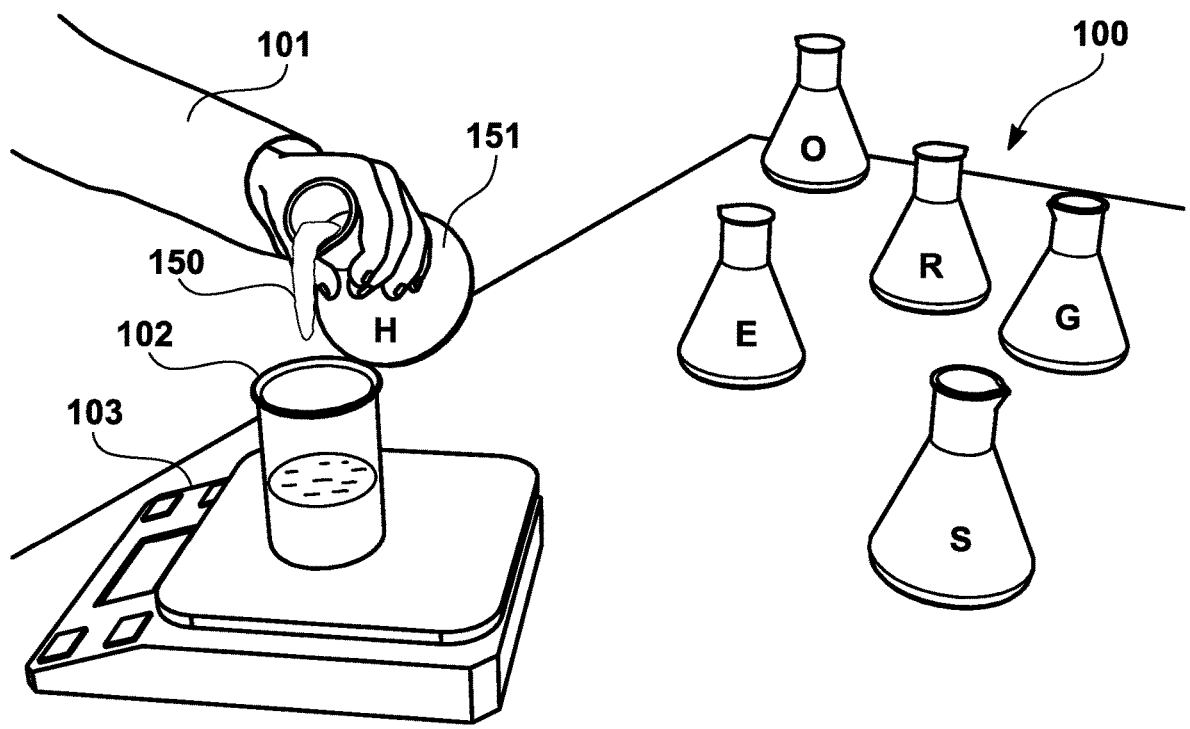
FIG. 1C illustrates the user adding hyaluronic acid to the beaker from a hyaluronic acid flask.
Figure 1D:
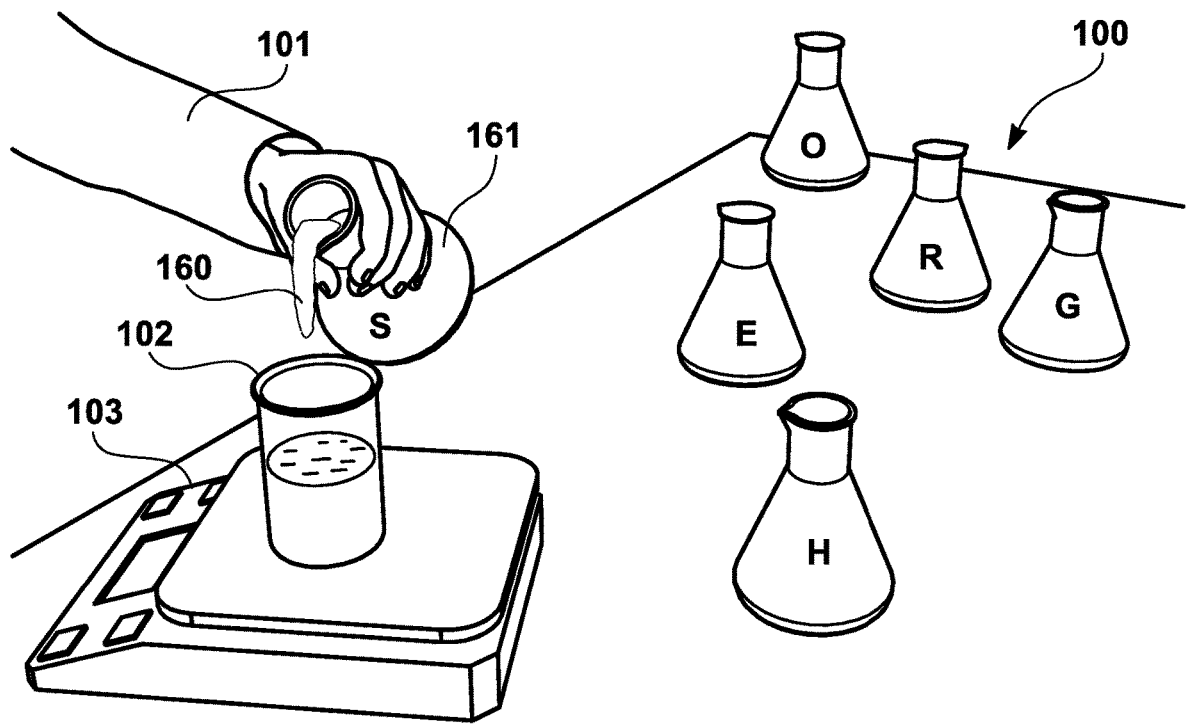
FIG. 1D illustrates the user adding a sunscreen composition to the beaker from a sunscreen composition beaker.
Figure 1E:
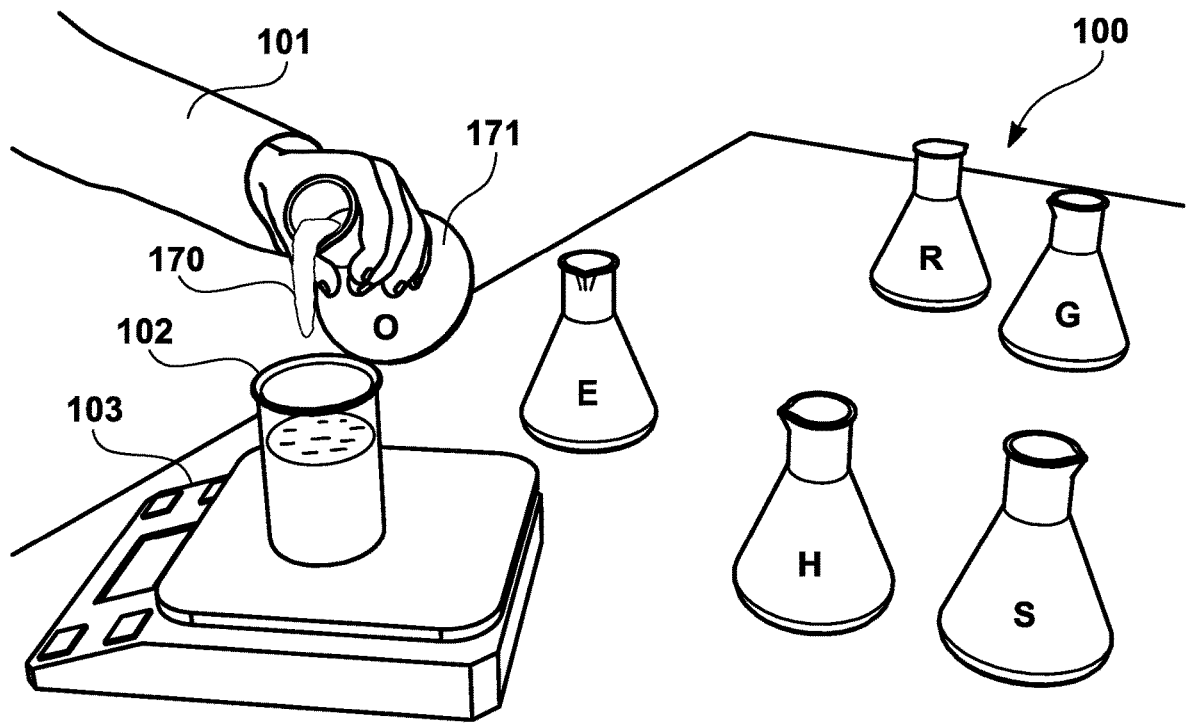
FIG. 1E illustrates the user adding a carrier agent, such as coconut oil, from an oil flask to the ingredients.
Figure 1F:
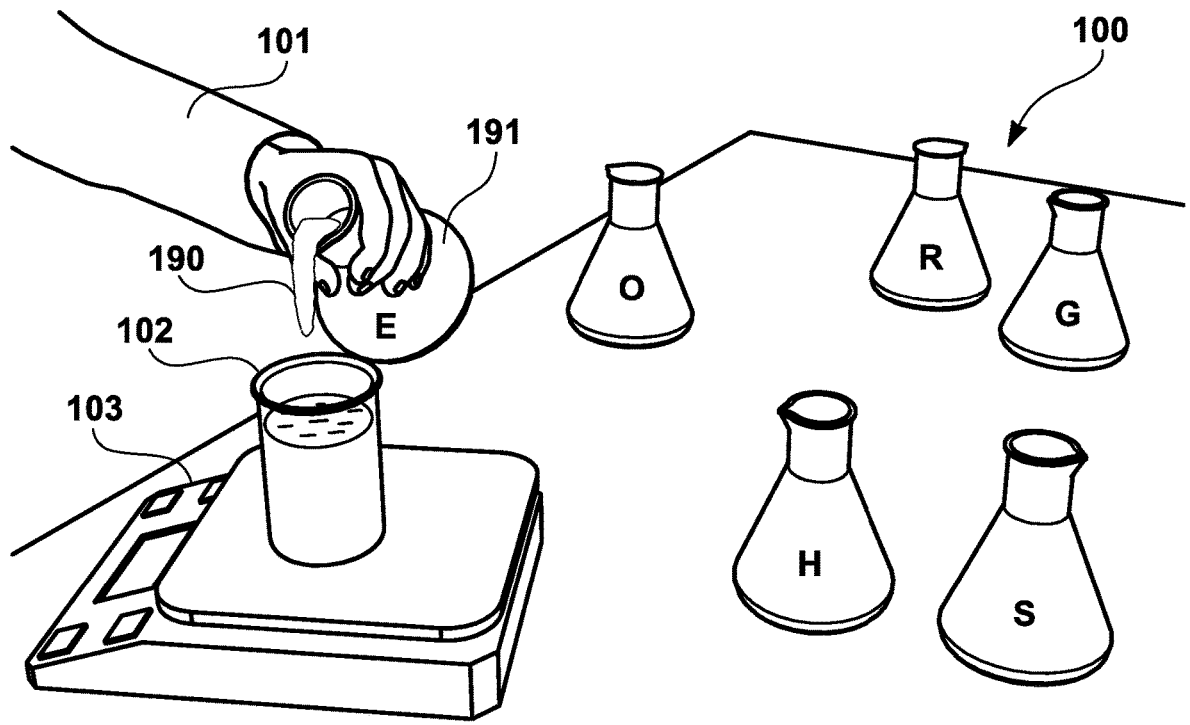
FIG. 1F illustrates the user adding an emulsifier to the beaker from an emulsifier flask.

FIGS. 1A-1F illustrate a laboratory environment 100 in which a user 101 (e.g., lab technician) prepares the skincare rejuvenation composition. In particular, FIG. 1A illustrates the user 101 weighing a beaker 102, having a solvent (e.g., water), on a scale 103 while pouring retinol 104 into the beaker 102 from a retinol flask 105. The weight determined by the scale 103 may be utilized to add an equal, or substantially equal, weight of other ingredients in the skincare rejuvenation composition. For instance, FIG. 1B illustrates the user 101 adding glycolic acid 110 to the beaker 102 from a glycolic acid flask 111. The amount of the glycolic acid 110 may the same, or substantially same, amount as the retinol 104 by weight percentage of the skincare rejuvenation composition. Additionally, FIG. 1C illustrates the user 101 adding hyaluronic acid 150 to the beaker 102 from a hyaluronic acid flask 151. The amount of the hyaluronic acid 150 may the same, or substantially same, amount as each of the retinol 104 and the glycolic acid 110 by weight percentage. FIG. 1D illustrates the user 101 adding a sunscreen composition 160 to the beaker 102 from a sunscreen composition flask 161. The sunscreen composition 160 may have been separately formulated in a different beaker than the beaker 102 utilized for blending the other ingredients of the skincare rejuvenation composition. Alternatively, the sunscreen composition 160 may have been a pre-formulated composition. FIG. 1E illustrates the user 101 adding a carrier agent, such as coconut oil 170, from an oil flask 171 to the ingredients. Finally, FIG. 1F illustrates the user 101 adding an emulsifier 190 to the beaker 161 from an emulsifier flask 191. The resulting skincare rejuvenation composition 172 is illustrated in the beaker 161.

The user 101 illustrated in FIGS. 1A-1F is intended to mean a user that uses the various laboratory equipment and chemicals to formulate the skincare rejuvenation composition, rather than an end-user of the skincare rejuvenation composition.

In one embodiment, the skincare rejuvenation composition is specifically formulated for application to the body of an end-user. Additionally, or alternatively, the skincare rejuvenation composition may be applied to the face of the end-user.

The selection of the carrier agent 170, such as coconut oil, may be based on adding thickness to skin texture.

Figure 2:
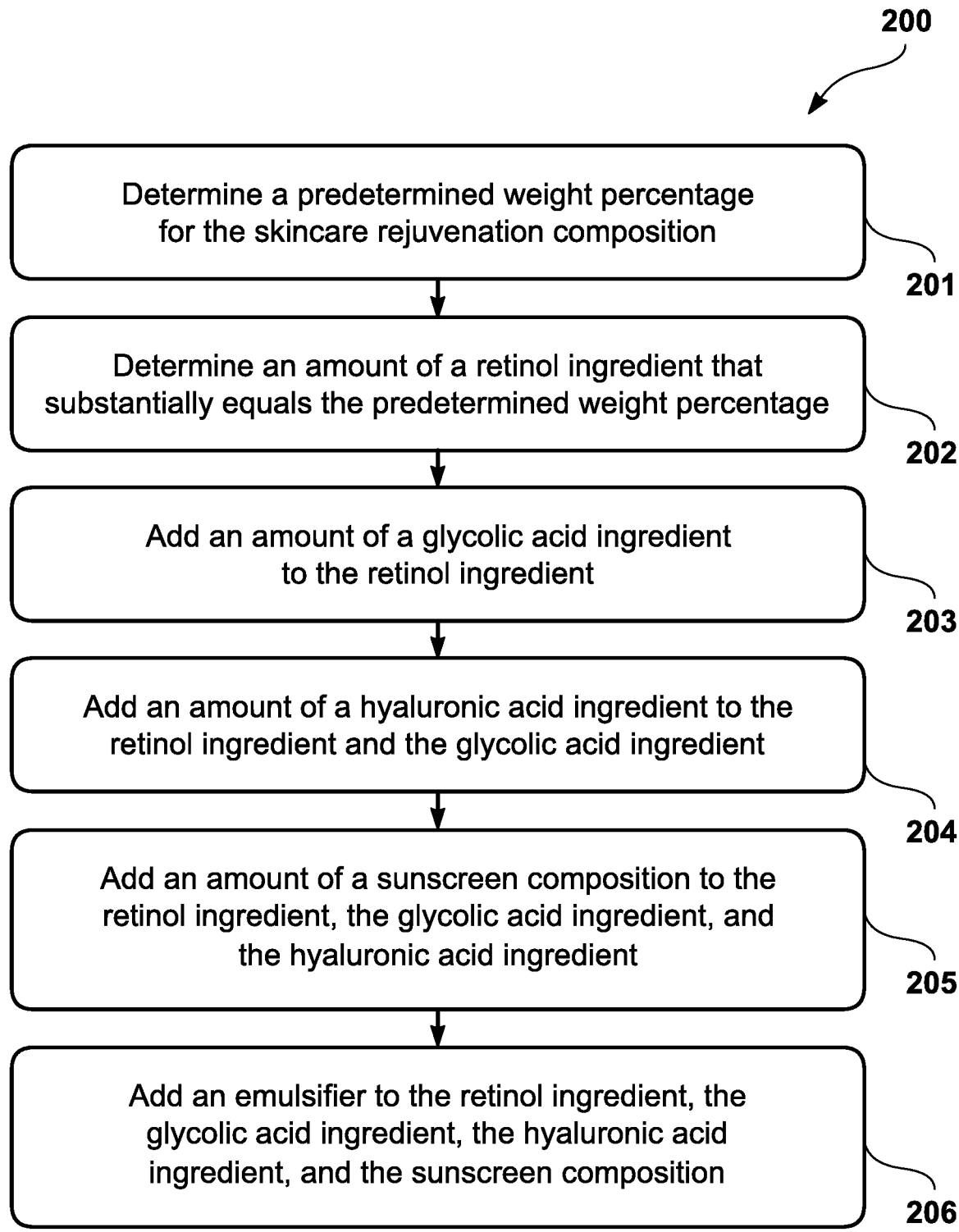
FIG. 2 illustrates a process that may be utilized to form the skincare rejuvenation composition.

FIG. 2 illustrates a process 200 that may be utilized to form the skincare rejuvenation composition. At a process block 201, the process 200 determines a predetermined weight percentage of the skincare rejuvenation composition. Furthermore, at a process block 202, the process 200 determines an amount of a retinol ingredient that substantially equals the predetermined weight percentage. In addition, at a process block 203, the process 200 adds an amount of a glycolic acid ingredient to the retinol ingredient. The amount of the glycolic acid ingredient substantially equals the predetermined weight percentage. At a process block 204, the process 200 adds an amount of a hyaluronic acid ingredient to the retinol ingredient and the glycolic acid ingredient. The amount of the hyaluronic acid ingredient substantially equals the predetermined weight percentage. Also, at a process block 205, the process 200 adds an amount of a sunscreen composition to the retinol ingredient, the glycolic acid ingredient, and the hyaluronic acid ingredient. Finally, at a process block 206, the process 200 adds an emulsifier to the retinol ingredient, the glycolic acid ingredient, the hyaluronic acid ingredient, and the sunscreen composition.

It is understood that the compositions and processes described herein may also be applied in other types of compositions and processes. Those skilled in the art will appreciate that the various adaptations and modifications of the embodiments of the compositions and processes described herein may be configured without departing from the scope and spirit of the present compositions and processes. Therefore, it is to be understood that, within the scope of the appended claims, the present compositions and processes may be practiced other than as specifically described herein.

I claim:

1. A skincare rejuvenation composition, adapted at least for tactile use, consisting of:
    a retinol having a first weight percentage;
    a glycolic acid having a second weight percentage that is substantially equal to the first weight percentage;
    a hyaluronic acid having a third weight percentage that is substantially equal to the first weight percentage and the second weight percentage such that the first weight percentage, the second weight percentage, and the third weight percentage are all substantially equal;
    a sunscreen composition consisting of titanium dioxide, zinc oxide, and avobenzone;
    an emulsifier; and
    a solvent.

2. The skincare rejuvenation composition of claim 1, wherein the sunscreen composition has an SPF substantially equal to thirty.

3. The skincare rejuvenation composition of claim 1, wherein the sunscreen composition has a fourth weight percentage that is substantially equal to the first weight percentage.

4. The skincare rejuvenation composition of claim 1, wherein the emulsifier has a fifth weight percentage that is greater than the first weight percentage.

5. The skincare rejuvenation composition of claim 1, wherein the emulsifier has a fifth weight percentage that is in a range of one to ten percent.

6. The skincare rejuvenation composition of claim 1, wherein the emulsifier is ionic.

7. The skincare rejuvenation composition of claim 1, wherein the emulsifier is non-ionic.

8. A skincare rejuvenation composition, adapted at least for tactile use, consisting of:
    a retinol having a first weight percentage;
    a glycolic acid having a second weight percentage that is substantially equal to the first weight percentage;
    a hyaluronic acid having a third weight percentage that is substantially equal to the first weight percentage and the second weight percentage such that the first weight percentage, the second weight percentage, and the third weight percentage are all substantially equal;
    a sunscreen composition consisting of titanium dioxide, zinc oxide, and avobenzone; and
    an emulsifier.

9. The skincare rejuvenation composition of claim 8, wherein the retinol is a skincare rejuvenation ingredient.

10. The skincare rejuvenation composition of claim 8, wherein the glycolic acid is a skin exfoliation ingredient, and wherein the hyaluronic acid is an acidity balancing ingredient.

11. A method of manufacture of a skincare rejuvenation composition, adapted at least for tactile use, comprising:
    determining a predetermined weight percentage for the skincare rejuvenation composition;
    determining an amount of a retinol that substantially equals the predetermined weight percentage;
    adding an amount of a glycolic acid to the retinol, the amount of the glycolic acid substantially equaling the predetermined weight percentage;
    adding an amount of a hyaluronic acid to the retinol and the glycolic acid, the amount of the hyaluronic acid substantially equaling the predetermined weight percentage;
    adding an amount of a sunscreen composition to the retinol, the glycolic acid, and the hyaluronic acid, the sunscreen composition consisting of: titanium dioxide, zinc oxide, and avobenzone; and
    adding an emulsifier to the retinol, the glycolic acid, the hyaluronic acid, and the sunscreen composition;
    wherein the skincare rejuvenation composition consists of: the retinol, the glycolic acid, the hyaluronic acid, the sunscreen composition, and the emulsifier.

12. The method of manufacture of claim 11, wherein the sunscreen composition has an SPF substantially equal to thirty.

13. The method of manufacture of claim 11, wherein the sunscreen composition has a weight percentage that is substantially equal to the predetermined weight percentage.

14. The method of manufacture of claim 11, wherein the emulsifier has a weight percentage that is greater than the predetermined weight percentage.

15. The method of manufacture of claim 11, wherein the emulsifier has a weight percentage that is in a range of one to ten percent.

16. The method of manufacture of claim 11, wherein the emulsifier is ionic.

17. The method of manufacture of claim 11, wherein the emulsifier is non-ionic.

* * * * *